(12) United States Patent
Linz et al.

(10) Patent No.: US 6,919,325 B2
(45) Date of Patent: Jul. 19, 2005

(54) PHARMACEUTICAL COMPOSITIONS CONTAINING TIOTROPIUM SALTS AND LOW-SOLUBILITY SALMETEROL SALTS

(75) Inventors: Guenter Linz, Mittelbiberach (DE); Rainer Soyka, Biberach (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 264 days.

(21) Appl. No.: 10/235,410

(22) Filed: Sep. 5, 2002

(65) Prior Publication Data

US 2003/0130300 A1 Jul. 10, 2003

Related U.S. Application Data

(60) Provisional application No. 60/387,060, filed on Jun. 7, 2002.

(30) Foreign Application Priority Data

Sep. 14, 2001 (DE) .......................... 101 45 438
Mar. 4, 2002 (DE) .......................... 102 09 243

(51) Int. Cl.$^7$ .................. A61K 31/60; A61K 31/44; A61K 31/34; A61K 31/19; A61K 31/135
(52) U.S. Cl. .................. 514/161; 514/291; 514/461; 514/568; 514/651
(58) Field of Search .................. 514/161, 291, 514/461, 568, 651

(56) References Cited

U.S. PATENT DOCUMENTS

| | | | |
|---|---|---|---|
| 4,042,700 A | 8/1977 | Banholzer et al. | |
| 4,608,377 A | 8/1986 | Banholzer et al. | |
| 4,783,534 A | 11/1988 | Banholzer et al. | |
| 5,610,163 A | 3/1997 | Banholzer et al. | |
| 5,654,314 A | 8/1997 | Banholzer et al. | |
| 5,770,738 A | 6/1998 | Banholzer et al. | |
| 5,952,505 A | 9/1999 | Banholzer et al. | |
| 6,413,497 B1 | 7/2002 | Weil et al. | |
| 6,433,027 B1 | 8/2002 | Bozung et al. | |
| 6,455,524 B1 | 9/2002 | Bozung et al. | |
| 6,482,429 B1 | 11/2002 | Etzler | |
| 6,486,321 B2 | 11/2002 | Banholzer et al. | |
| 6,506,900 B1 | 1/2003 | Banholzer et al. | |
| 6,630,466 B2 | 10/2003 | Bozung et al. | |
| 2002/0115681 A1 | 8/2002 | Bozung et al. | |
| 2002/0133010 A1 | 9/2002 | Banholzer et al. | |
| 2002/0193392 A1 | 12/2002 | Schmelzer et al. | |
| 2003/0069310 A1 | 4/2003 | Linz et al. | |
| 2004/0010003 A1 * | 1/2004 | Banholzer et al. | .......... 514/291 |

FOREIGN PATENT DOCUMENTS

DE 198 47 970 A1 4/2000

OTHER PUBLICATIONS

U.S. Appl. No. 10/736,264, filed Dec. 15, 2003, entitled Powered Medicaments Containing a Tiotropium Salt and Salmeterol Xinafoate.
Wolfe, James et al; Comparison of powder and aerosol formulations of salmeterol in the treatment of asthma; Chemical Abstract 132:284088 (2000).
U.S. Appl. No. 10/054,567—Pharmaceutical Compositions based on Tiotropium Salts of Salts of Salmeterol—filed Nov. 13, 2001.
U.S. Appl. No. 09/568,880—New Medicament Compositions Based on Anticholinergically–effective Compounds and betamimetics—filed May 9, 2000.

* cited by examiner

Primary Examiner—Raymond J. Henley III
(74) Attorney, Agent, or Firm—Michael P. Morris; Mary-Ellen M. Devlin; Andrea D. Small

(57) ABSTRACT

Pharmaceutical compositions and kits comprising:
  (a) a tiotropium salt; and
  (b) a salmeterol salt having a solubility in water of 0.1 mg/mL or less,
processes for preparing them, and their use in the treatment of respiratory complaints, asthma, and chronic obstructive pulmonary disease (COPD).

23 Claims, 1 Drawing Sheet

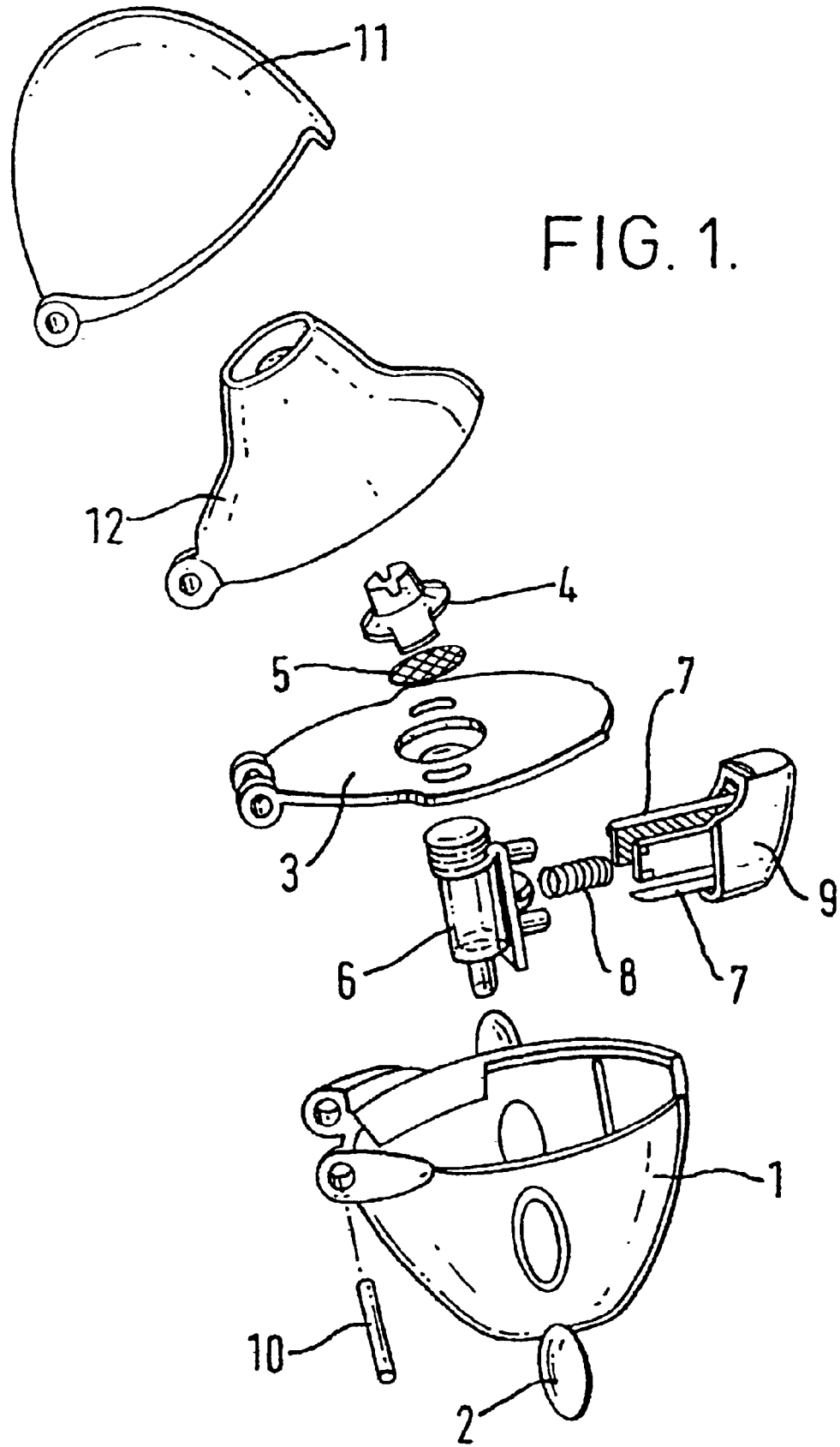

PHARMACEUTICAL COMPOSITIONS CONTAINING TIOTROPIUM SALTS AND LOW-SOLUBILITY SALMETEROL SALTS

RELATED APPLICATIONS

Benefit under 35 U.S.C. § 119(e) of prior provisional application Ser. No. 60/387,060, filed Jun. 6, 2002, is hereby claimed.

FIELD OF THE INVENTION

The present invention relates to new pharmaceutical compositions for inhalation based on tiotropium salts and salts of salmeterol which do not dissolve easily, process for preparing them, and their use in the treatment of respiratory complaints.

BACKGROUND OF THE INVENTION

The compound tiotropium bromide, a salt of tiotropium, is known from European Patent Application EP 418 716 A1 and has the following chemical structure:

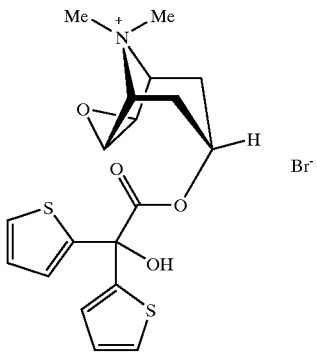

This compound can also be known by the chemical name (1α,2β,4β,5α,7β)-7-[(hydroxydi-2-thienylacetyl)oxy]-9,9-dimethyl-3-oxa-9-azoniatricyclo[3.3.1.0$^{2,4}$]nonane bromide and has valuable pharmacological properties. The term tiotropiun should be understood within the scope of the present invention as being a reference to the free cation.

Like other salts of tiotropium, it is a highly effective anticholinergic and can therefore provide therapeutic benefit in the treatment of asthma or chronic obstructive pulmonary disease (COPD).

Tiotropium salts are preferably administered by inhalation. Suitable inhalable powders packed into appropriate capsules (inhalettes) may be used, administered by means of corresponding powder inhalers. Alternatively, they may be administered by the use of suitable inhalable aerosols. These also include powdered inhalable aerosols which contain, for example, HFA134a, HFA227, or mixtures thereof as propellant gas. They may also be administered in the form of suitable solutions of the tiotropium salt.

BRIEF DESCRIPTION OF THE DRAWINGS

FIG. 1: Preferred inhaler for using the pharmaceutical combination according to the invention, this inhaler (HANDIHALER®) for inhaling powdered pharmaceutical compositions from capsules is characterized by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut.

DETAILED DESCRIPTION OF THE INVENTION

Surprisingly, an unexpectedly beneficial therapeutic effect, particularly a synergistic effect can be observed in the treatment of inflammatory or obstructive respiratory complaints if one or more, preferably one, anticholinergic is used with one or more corticosteroids; and one or more tiotropium salts 1 are used in conjunction with one or more salmeterol salts 2 which do not readily dissolve, the salmeterol salts 2 having a solubility in water of 0.1 mg/mL or less, preferably 0.05 mg/mL or less, most preferably 0.035 mg/mL or less. These salmeterol salts 2 used within the scope of the present invention are characterized in particular by being very well tolerated locally.

This significantly reduces undesirable side effects, for example, which are frequently observed when β-mimetics, such as salmeterol, are administered to humans. Examples of central side effects of β-mimetics include, for example, general malaise, excitement, sleeplessness, anxiety, trembling fingers, sweating, and headaches.

Accordingly, the present invention relates to combinations of pharmaceutical compositions characterized in that that contain one or more, preferably one, tiotropium salt 1 in combination with one or more, preferably one salmeterol salt 2 of limited solubility, the salmeterol salt 2 having a solubility in water of 0.1 mg/mL or less, preferably 0.05 mg/mL or less, most preferably 0.035 mg/mL or less.

The term tiotropium is intended within the scope of the present invention as a reference to the free cation 1'. Any reference to salmeterol is intended within the scope of the present invention as a reference to the free base 2'. The preparation of salmeterol was first described in British Patent GB 2140800 to the content of which reference is hereby made.

The active substance combinations according to the invention are surprisingly also characterized both by a rapid onset of activity and by their long-lasting effect. This is very important to the patient as on the one hand they will rapidly experience an improvement in their condition after taking the combination and on the other hand because of the long-lasting effect it is sufficient to take the drug once a day.

The abovementioned effects are observed both when the two active substances are taken simultaneously in a single active substance formulation and when they are administered successively in separate formulations. It is preferable according to the invention to administer the two active substance ingredients simultaneously in a single formulation.

In one aspect the present invention relates to a pharmaceutical composition which contains one or more tiotropium salts 1 and one or more salmeterol salts 2, optionally in the form of their solvates or hydrates. The active substances may either be combined in a single preparation or contained in two separate formulations. Pharmaceutical compositions which contain the active substances 1 and 2 in a single preparation are preferred according to the invention.

In another aspect the present invention relates to a pharmaceutical composition which contains, in addition to therapeutically effective quantities of 1 and 2, a pharmaceutically acceptable excipient. In one aspect the present invention relates to a pharmaceutical composition which does not contain any pharmaceutically acceptable excipient in addition to therapeutically effective quantities of 1 and 2.

The present invention also relates to the use of 1 and 2 for preparing a pharmaceutical composition containing therapeutically effective quantities of 1 and 2 for treating inflammatory or obstructive diseases of the respiratory tract, particularly asthma and/or COPD, by simultaneous or successive administration.

The present invention also relates to the simultaneous or successive use of therapeutically effective doses of the combination of the above pharmaceutical compositions 1 and 2 for treating inflammatory or obstructive diseases of the respiratory tract, particularly asthma or COPD.

By the tiotropium salts 1 which may be used within the scope of the present invention are meant the compounds which contain, in addition to tiotropium as counter-ion (anion), chloride, bromide, iodide, methanesulfonate, p-toluenesulfonate or methyl sulfate. Within the scope of the present invention, the methanesulfonate, chloride, bromide and iodide are preferred of all the tiotropium salts 1, the methanesulfonate and bromide being of particular importance. Of outstanding importance according to the invention is tiotropium bromide. The tiotropium salts 1 may optionally be used in the form of their solvates and hydrates. The hydrates are particularly preferably used. Of all the hydrates of the tiotropium salts 1 which may be used according to the invention, the crystalline tiotropium bromide monohydrate described in WO 02/30928 is particularly preferred within the scope of the present invention, and WO 02/30928 is hereby incorporated herein by reference in its entirety.

By salts of salmeterol 2 of limited solubility are meant, according to the invention, pharmaceutically acceptable salts of salmeterol which have a solubility in water of 0.1 mg/mL or less, preferably 0.05 mg/mL or less, most preferably 0.035 mg/mL or less.

Salmeterol has a chiral center. The present invention includes the salts 2 in racemic or enantiomerically pure form. Both the (R)-enantiomer and the (S)-enantiomer are particularly important. Moreover, within the scope of the present invention, the salts 2 may be used in the form of the non-racemic mixtures of the two enantiomers.

The salmeterol salts 1 may be prepared from the free base of salmeterol according or analogously to methods known in the art for forming acid addition salts. These comprise reacting the free base salmeterol 2' with the corresponding carboxylic acids in suitable solvents, preferably in organic solvents. For this purpose the desired acid is preferably first taken up in an organic solvent, most preferably a solvent selected from among ethyl acetate, methanol, ethanol, isopropanol and diethylether or mixtures thereof. The abovementioned solvents may optionally also be used in admixture with tert-butylmethylether or cyclohexane. The acids taken up in one of the abovementioned solvents may optionally be dissolved by heating, preferably by heating up to the boiling temperature of the solvent. Salmeterol 2', optionally dissolved in one of the abovementioned solvents, is added to this solution. The salts 2 are crystallized out of the resulting solution, optionally with cooling, and isolated.

According to the invention the salmeterol salts 2 of limited solubility

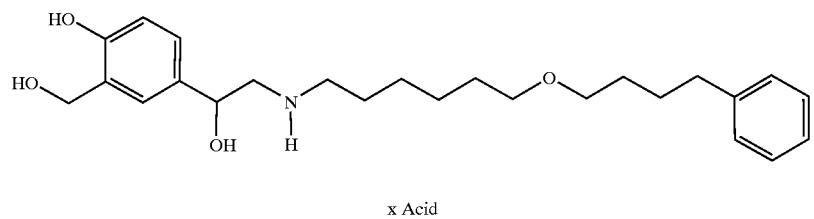

x Acid selected from among:
4-hydroxy-α¹-[[[6-(4-phenylbutoxy)hexyl]amino]methyl]-1,3-benzenedimethanolbiphenyl-4-carboxylate salt;
4-hydroxy-α¹-[[[6-(4-phenylbutoxy)hexyl]amino]methyl]-1,3-benzenedimethanol-4-chlorosalicylate salt;
4-hydroxy-α¹-[[[6-(4-phenylbutoxy)hexyl]amino]methyl]-1,3-benzenedimethanol-2,4-dihydroxybenzoate salt;
4-hydroxy-α¹-[[[6-(4-phenylbutoxy)hexyl]amino]methyl]-1,3-benzenedimethanol-2-hydroxy-3-naphthoate salt;
4-hydroxy-α¹-[[[6-(4-phenylbutoxy)hexyl]amino]methyl]-1,3-benzenedimethanol-1-hydroxy-2-naphthoate salt; and
4-hydroxy-α¹-[[[6-(4-phenylbutoxy)hexyl]amino]methyl]-1,3-benzenedimethanolsalicylate salt, are preferred.

Other salmeterol salts 2 of limited solubility according to the invention which may be used in the pharmaceutical combinations according to the invention are those salts which are obtained by reacting the free base of salmeterol 2' with one or more, preferably one of the acids in Table 1.

TABLE 1

| Acid | Solvent (for salt formation) | Melting Point of 2 (° C., by DSC) |
| --- | --- | --- |
| 2-hydroxy-1-naphthoic acid | ethyl acetate | 122 |
| 3,5-dichlorosalicylic acid | diethyl ether | 108 |
| furan-2-carboxylic acid | diethyl ether | 80 |
| 0.5 equiv. of 2,5-dihydroxyterephthalic acid | ethyl acetate | 102 |
| cinnamic acid | ethyl acetate | 89 |
| triphenylacetic acid | diethyl ether | 116 |
| 4-phenylcinnamic acid | ethyl acetate | 109 |
| biphenyl-2-carboxylic acid | ethyl acetate | 127 |
| 4-trifluoromethylcinnamic acid | ethyl acetate | 125 |
| 9-fluorenylideneacetic acid | ethyl acetate | 88 |
| 3-(2-naphthyl)acrylic acid | ethyl acetate | 97 |
| 3-(1-naphthyl)acrylic acid | ethyl acetate | 77 |
| 1-naphthoic acid | ethyl acetate | 120 |
| 2,6-dichlorobenzoic acid | ethyl acetate | 103 |
| 3,4-dichlorobenzoic acid | ethyl acetate | 115 |
| 3,5-dichlorobenzoic acid | ethyl acetate | 110 |
| 4-bromobenzoic acid | ethyl acetate | 115 |
| 4-trifluoromethylbenzoic acid | ethyl acetate | 125 |
| 4-isopropylbenzoic acid | ethyl acetate | 85–90 |
| 4-tert-butylbenzoic acid | ethyl acetate | 95 |
| 3-(3-indolyl)acrylic acid | ethyl acetate | 113 |
| 2,4-dichlorocinnamic acid | ethyl acetate | 138 |
| 2,6-dichlorocinnamic acid | ethyl acetate | 82 |
| 2,5-dimethoxycinnamic acid | ethyl acetate | 88 |

TABLE 1-continued

| Acid | Solvent (for salt formation) | Melting Point of 2 (° C., by DSC) |
|---|---|---|
| 2-trifluoromethylcinnamic acid | ethyl acetate | 94 |
| 3-trifluoromethylcinnamic acid | ethyl acetate | 92 |
| 3-chlorocinnamic acid | ethyl acetate | 90 |
| 3,4-dichlorocinnamic acid | ethyl acetate | 116 |
| 4-bromocinnamic acid | ethyl acetate | 127 |
| 4-chlorocinnamic acid | ethyl acetate | 123 |
| 4-methoxycinnamic acid | ethyl acetate | 98 |
| 4-fluorocinnamic acid | ethyl acetate | 113 |
| 4-isopropylcinnamic acid | ethyl acetate | 82 |
| 4-tert-butylcinnamic acid | ethyl acetate | 93 |
| 2,6-difluorocinnamic acid | ethyl acetate | 77 |
| 2,4-difluorocinnamic acid | ethyl acetate | 121 |
| 3,4-difluorocinnamic acid | ethyl acetate | 102 |
| 2,4,5-trifluorocinnamic acid | ethyl acetate | 120 |
| 3,4,5-trifluorocinnamic acid | ethyl acetate | 107 |
| 3-methoxysalicylic acid | ethyl acetate | 118 |
| 4-methoxysalicylic acid | ethyl acetate | 113 |
| 5-methoxysalicylic acid | ethyl acetate | 114 |
| 4-methylsalicylic acid | ethyl acetate | 116 |
| 5-aminosalicylic acid | ethyl acetate/ isopropanol | 146 |
| 3-chlorosalicylic acid | ethyl acetate | 108 |
| 5-sulfosalicylic acid | ethyl acetate/ isopropanol | 129 |
| 5-acetylsalicylic acid | ethyl acetate | 80 |
| 3,5-diiodosalicylic acid | ethyl acetate | 133 |
| isoquinoline-1-carboxylic acid | ethyl acetate | 105 |
| 9-fluorenecarboxylic acid | ethyl acetate | 90 |
| 9-fluorenone-1-carboxylic acid | ethyl acetate | 136 |
| 3,5-diisopropylsalicylic acid | ethyl acetate | 115 |
| diflunisal | ethyl acetate | 104 |

Of particular importance according to the invention are pharmaceutical combinations of the salmeterol salts 2 of limited solubility within the scope of the invention, selected from among:

4-hydroxy-α$^1$-[[[6-(4-phenylbutoxy)hexyl]amino]methyl]-1,3-benzenedimethanol-4-phenylcinnamate salt 2.1:

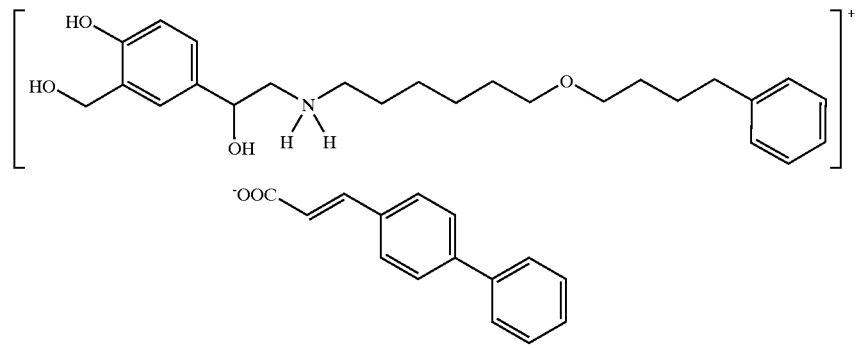

1.35 g (6 mmol) of 4-phenylcinnamic acid is dissolved by refluxing in 75 mL of ethyl acetate. To this solution is added a warm solution of 2.5 g (6 mmol) of salmeterol in 25 mL of ethyl acetate. The solution is left to cool and stirred for 16 hours at ambient temperature. The suspension is filtered, the precipitate is washed with ethyl acetate and tert-butylmethylether and dried in vacuo at 25° C.–30° C. 3.47 g of the title compound are obtained as a colorless solid. Melting point: 109° C.

The following compounds were prepared analogously:

4-hydroxy-α$^1$-[[[6-(4-phenylbutoxy)hexyl]amino]methyl]-1,3-benzenedimethanol-4-trifluoromethylcinnamate salt 2.2, melting point: 125° C.;

4-hydroxy-α$^1$-[[[6-(4-phenylbutoxy)hexyl]amino]methyl]-1,3-benzenedimethanol-3,4-dichlorocinnamate salt 2.3, melting point: 116° C.;

4-hydroxy-α$^1$-[[[6-(4-phenylbutoxy)hexyl]amino]methyl]-1,3-benzenedimethanol-2,4-dichlorocinnamate salt 2.4, melting point: 183° C.;

4-hydroxy-α$^1$-[[[6-(4-phenylbutoxy)hexyl]amino]methyl]-1,3-benzenedimethanolcinnamate salt 2.5, melting point: 89° C.;

4-hydroxy-α$^1$-[[[6-(4-phenylbutoxy)hexyl]amino]methyl]-1,3-benzenedimethanol-3-(2-naphthyl)acrylate salt 2.6, melting point: 97° C.;

4-hydroxy-α$^1$-[[[6-(4-phenylbutoxy)hexyl]amino]methyl]-1,3-benzenedimethanol-3-(1-naphthyl)acrylate salt 2.7, melting point: 77° C.;

4-hydroxy-α$^1$-[[[6-(4-phenylbutoxy)hexyl]amino]methyl]-1,3-benzenedimethanol-2,6-dichlorocinnamate salt 2.8, melting point: 82° C.;

4-hydroxy-α$^1$-[[[6-(4-phenylbutoxy)hexyl]amino]methyl]-1,3-benzenedimethanol-2,5-dimethoxycinnamate salt 2.9, melting point: 88° C.;

4-hydroxy-α$^1$-[[[6-(4-phenylbutoxy)hexyl]amino]methyl]-1,3-benzenedimethanol-2-trifluoromethylcinnamate salt 2.10, melting point: 94° C.;

4-hydroxy-α$^1$-[[[6-(4-phenylbutoxy)hexyl]amino]methyl]-1,3-benzenedimethanol-3-trifluoromethylcinnamate salt 2.11, melting point: 92° C.;

4-hydroxy-α$^1$-[[[6-(4-phenylbutoxy)hexyl]amino]methyl]-1,3-benzenedimethanol-3-chlorocinnamate salt 2.12, melting point: 90° C.;

4-hydroxy-α$^1$-[[[6-(4-phenylbutoxy)hexyl]amino]methyl]-1,3-benzenedimethanol-4-bronocinnamate salt 2.13, melting point: 127° C.;

4-hydroxy-α$^1$-[[[6-(4-phenylbutoxy)hexyl]amino]methyl]-1,3-benzenedimethanol-4-chlorocinnamate salt 2.14, melting point: 123° C.;

4-hydroxy-α$^1$-[[[6-(4-phenylbutoxy)hexyl]amino]methyl]-1,3-benzenedimethanol-4-methoxycinnamate salt 2.15, melting point: 98° C.;

4-hydroxy-α$^1$-[[[6-(4-phenylbutoxy)hexyl]amino]methyl]-1,3-benzenedimethanol-4-fluorocinnamate salt 2.16, melting point: 113° C.;

4-hydroxy-α$^1$-[[[6-(4-phenylbutoxy)hexyl]amino]methyl]-1,3-benzenedimethanol-4-isopropylcinnamate salt 2.17, melting point: 82° C.;

4-hydroxy-α¹-[[[6-(4-phenylbutoxy)hexyl]amino]methyl]-1,3-benzenedimethanol-4-tert-butylcinnamate salt 2.18, melting point: 93° C.;

4-hydroxy-α¹-[[[6-(4-phenylbutoxy)hexyl]amino]methyl]-1,3-benzenedimethanol-2,4-difluorocinnamate salt 2.19, melting point: 121° C.;

4-hydroxy-α¹-[[[6-(4-phenylbutoxy)hexyl]amino]methyl]-1,3-benzenedimethanol-3,4-difluorocinnamate salt 2.20, melting point: 102° C.;

4-hydroxy-α¹-[[[6-(4-phenylbutoxy)hexyl]amino]methyl]-1,3-benzenedimethanol-2,4,5-trifluorocinnamate salt 2.21, melting point: 120° C.; and 4-hydroxy-α¹-[[[6-(4-phenylbutoxy)hexyl]amino]methyl]-1,3-benzenedimethanol-3,4,5-trifluorocinnamate salt 2.22, melting point: 107° C.

Of equal importance according to the invention are pharmaceutical combinations of the salmeterol salts 2 of limited solubility within the scope of the invention, selected from among:

4-hydroxy-α¹-[[[6-(4-phenylbutoxy)hexyl]amino]methyl]-1,3-benzenedimethanol-5-(2,4-difluorophenyl)salicylate salt 2.23

4-hydroxy-α¹-[[[6-(4-phenylbutoxy)hexyl]amino]methyl]-1,3-benzenedimethanol-4-methylsalicylate salt 2.31, melting point: 116° C.;

4-hydroxy-α¹-[[[6-(4-phenylbutoxy)hexyl]amino]methyl]-1,3-benzenedimethanol-5-aminosalicylate salt 2.32, melting point: 146° C.;

4-hydroxy-α¹-[[[6-(4-phenylbutoxy)hexyl]amino]methyl]-1,3-benzenedimethanol-3-chlorosalicylate salt 2.33, melting point: 108° C.;

4-hydroxy-α¹-[[[6-(4-phenylbutoxy)hexyl]amino]methyl]-1,3-benzenedimethanol-5-sulfosalicylate salt 2.34, melting point: 129° C.;

4-hydroxy-α¹-[[[6-(4-phenylbutoxy)hexyl]amino]methyl]-1,3-benzenedimethanol-5-acetylsalicylate salt 2.35, melting point: 80° C.; and 4-hydroxy-α¹-[[[6-(4-phenylbutoxy)hexyl]amino]methyl]-1,3-benzenedimethanol-3,5-diiodosalicylate salt 2.36, melting point: 133° C.

In the abovementioned salts according to the invention the base salmeterol and the acid used in each case are present in a molar ratio of salmeterol:acid of 1:1, unless otherwise stated.

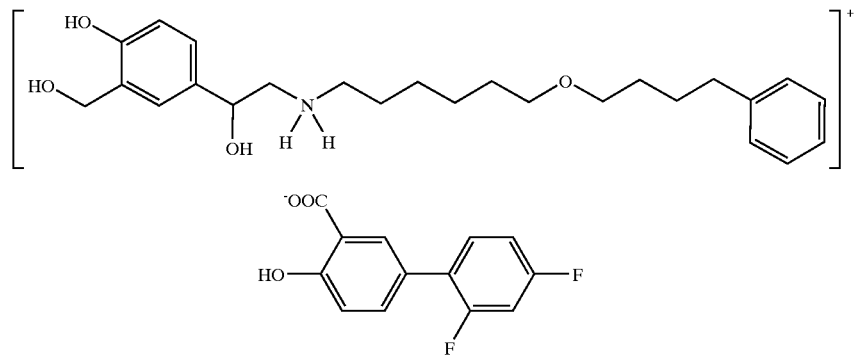

30 g salmeterol is dissolved by refluxing in 300 mL of ethyl acetate. To this solution are added 18.3 g of 5-(2,4-difluorophenyl)salicylic acid (Diflunisal). The solution is left to cool to ambient temperature. The suspension is filtered off, the precipitate is washed with ethyl acetate and dried at 35° C. in vacuo. 46 g of the title salt are obtained as a colorless solid. Melting point: 104° C.

The following compounds were prepared analogously:

4-hydroxy-α¹-[[[6-(4-phenylbutoxy)hexyl]amino]methyl]-1,3-benzenedimethanol-3,5-diisopropylsalicylate salt 2.24, melting point: 115° C.;

4-hydroxy-α¹-[[[6-(4-phenylbutoxy)hexyl]amino]methyl]-1,3-benzenedimethanol-4-chlorosalicylate salt 2.25, melting point: 123° C.;

4-hydroxy-α¹-[[[6-(4-phenylbutoxy)hexyl]amino]methyl]-1,3-benzenedimethanol-3,5-dichlorosalicylate salt 2.26, melting point: 108° C.;

4-hydroxy-α¹-[[[6-(4-phenylbutoxy)hexyl]amino]methyl]-1,3-benzenedimethanol-2,5-dihydroxyterephthalate salt 2.27 (base:acid (1:2)), melting point: 102° C.;

4-hydroxy-α¹-[[[6-(4-phenylbutoxy)hexyl]amino]methyl]-1,3-benzenedimethanol-3-methoxysalicylate salt 2.28, melting point: 118° C.;

4-hydroxy-α¹-[[[6-(4-phenylbutoxy)hexyl]amino]methyl]-1,3-benzenedimethanol-4-methoxysalicylate salt 2.29, melting point: 113° C.;

4-hydroxy-α¹-[[[6-(4-phenylbutoxy)hexyl]amino]methyl]-1,3-benzenedimethanol-5-methoxysalicylate salt 2.30, melting point: 114° C.;

The identity of the abovementioned compounds was confirmed by ¹H-NMR-spectroscopy and ESI mass spectrometry.

In the active substance combinations of 1 and 2 according to the invention, ingredients 1 and 2 may be present in the form of their enantiomers, mixtures of enantiomers or in the form of racemates.

The proportions in which the active substances 1 and 2 may be used in the active substance combinations according to the invention are variable. Active substances 1 and 2 may possibly be present in the form of their solvates or hydrates. Depending on the choice of the compounds 1 and 2, the weight ratios which may be used within the scope of the present invention vary on the basis of the different molecular weights of the various salt forms. The weight ratios given below were therefore based on the tiotropium cation 1' and the free base of salmeterol 2'. The active substance combinations according to the invention may contain 1' and 2' in ratios by weight ranging from 1:300 to 30:1, preferably from 1:230 to 20:1, more preferably from 1:150 to 10:1, more preferably from 1:50 to 5:1, most preferably from 1:35 to 2:1. Of particular interest according to the invention are pharmaceutical compositions containing the combination of 1' and 2' in a weight ratio in the range from 1:25 to 1:1, preferably in the range from 1:10 to 1:2, most preferably in the range from 1:5 to 1:2.5.

For example and without restricting the scope of the invention thereto, preferred combinations of 1 and 2 according to the invention may contain tiotropium 1' and salmeterol 2' in the following weight ratios: 1:40; 1:20; 1:11.1; 1:10; 1:5.6; 1:5; 1:2.8; 1:2.5; 1:1.4; 1:1.25; 1.44:1; and 1.6:1.

The pharmaceutical compositions according to the invention containing the combinations of 1 and 2 are preferably prepared by administering tiotropium 1' and salmeterol 2' together in doses of 0.01 μg to 10000 μg, preferably from 0.1 μg to 2000 μg, more preferably from 1 μg to 1000 μg, preferably also from 5 μg to 500 μg, preferably according to the invention from 10 μg to 200 μg, preferably from 20 μg to 100 μg, most preferably from 30 μg to 70 μg per single dose.

For example, combinations of 1 and 2 according to the invention contain an amount of tiotropium 1' and salmeterol 2' such that the total dosage per single dose is 30 μg, 35 μg, 45 μg, 55 μg, 60 μg, 65 μg, 90 μg, 105 μg, 110 μg, 140 μg, or similar. In these ranges, the active substances 1' and 2' are present in the weight ratios described hereinbefore.

For example and without restricting the scope of the invention thereto, the combinations of 1 and 2 according to the invention may contain an amount of tiotropium 1' and salmeterol 2' such that in each individual dose 5 μg of 1' and 25 μg of 2', 5 μg of 1' and 50 μg of 2', 5 μg of 1' and 100 μg of 2', 5 μg of 1' and 200 μg of 2', 10 μg of 1' and 25 μg of 2', 10 μg of 1' and 50 μg of 2', 10 μg of 1' and 100 μg of 2', 10 μg of 1' and 200 μg of 2', 18 μg of 1' and 25 μg of 2', 18 μg of 1' and 50 μg of 2', 18 μg of 1' and 100 μg of 2', 18 μg of 1' and 200 μg of 2', 20 μg of 1' and 25 μg of 2', 20 μg of 1' and 50 μg of 2', 20 μg of 1' and 100 μg of 2', 20 μg of 1' and 200 μg of 2', 36 μg of 1' and 25 μg of 2', 36 μg of 1' and 50 μg of 2', 36 μg of 1' and 100 μg of 2', 36 μg of 1' and 200 μg of 2', 40 μg of 1' and 25 μg of 2', 40 μg of 1' and 50 μg of 2', 40 μg of 1' and 100 μg of 2', or 40 μg of 1' and 200 μg of 2' are administered.

If the active substance combination wherein 1 denotes tiotropium bromide and 2 denotes one of the particularly preferred salts 2, salmeterol-4-phenylcinnamate (2.1), is used as the preferred combination of 1 and 2 according to the invention, the quantities of active substances 1' and 2' administered per single dose as mentioned above by way of example correspond to the following quantities of 1 and 2 administered per single dose: 6 μg of 1 and 38.49 μg of 2, 6 μg of 1 and 76.98 μg of 2, 6 μg of 1 and 153.96 μg of 2, 6 μg of 1 and 307.92 μg of 2, 12 μg of 1 and 38.49 μg of 2, 12 μg of 1 and 76.98 μg of 2, 12 μg of 1 and 153.96 μg of 2, 12 μg of 1 and 307.92 μg of 2, 21.7 μg of 1 and 38.49 μg of 2, 21.7 μg of 1 and 76.98 μg of 2, 21.7 μg of 1 and 153.96 μg of 2, 21.7 μg of 1 and 307.92 μg of 2, 24.1 μg of 1 and 38.49 μg of 2, 24.1 μg of 1 and 76.98 μg of 2, 24.1 μg of 1 and 153.96 μg of 2, 24.1 μg of 1 and 307.92 μg of 2, 43.3 μg of 1 and 38.49 μg of 2, 43.3 μg of 1 and 76.98 μg of 2, 43.3 μg of 1 and 153.96 μg of 2, 43.3 μg of 1 and 307.92 μg of 2, 48.1 μg of 1 and 38.49 μg of2, 48.1 μg of 1 and 76.98 μg of 2, 48.1 μg of 1 and 153.96 μg of 2, or 48.1 μg of 1 and 307.92 μg of 2.

If in the preferred combination of 1 and 2 according to the invention wherein 2 denotes one of the particularly preferred salts 2, salmeterol-4-phenylcinnamate (2,1), tiotropium bromide monohydrate is used as component 1, for example, the quantities of active substances 1' and 2' administered per single dose as mentioned above by way of example correspond to the following quantities of 1 and 2 administered per single dose: 6.2 μg of 1 and 38.49 μg of 2, 6.2 μg of 1 and 76.98 μg of 2, 6.2 μg of 1 and 153.96 μg of 2, 6.2 μg of 1 and 307.92 μg of 2, 12.5 μg of 1 and 38.49 μg of 2, 12.5 μg of 1 and 76.98 μg of 2, 12.5 μg of 1 and 153.96 μg of 2, 12.5 μg of 1 and 307.92 μg of 2, 22.5 μg of 1 and 38.49 μg of 2, 22.5 μg of 1 and 76.98 μg of 2, 22.5 μg of 1 and 153.96 μg of 2, 22.5 μg of 1 and 307.92 μg of 2, 25 μg of 1 and 38.49 μg of 2, 25 μg of 1 and 76.98 μg of 2, 25 μg of 1 and 153.96 μg of 2, 25 μg of 1 and 307.92 μg of 2, 45 μg of 1 and 38.49 μg of 2, 45 μg of 1 and 76.98 μg of 2, 45 μg of 1 and 153.96 μg of 2, 45 μg of 1 and 307.92 μg of 2, 50 μg of 1 and 38.49 μg of 2, 50 μg of 1 and 76.98 μg of 2, 50 μg of 1 and 153.96 μg of 2, or 50 μg of 1 and 307.92 μg of 2.

The active substance combinations of 1 and 2 according to the invention are preferably administered by inhalation. For this purpose, ingredients 1 and 2 have to be made available in forms suitable for inhalation. Inhalable preparations include inhalable powders, in particular. Inhalable powders according to the invention containing the combination of active substances 1 and 2 may consist of the active substances on their own or of a mixture of the active substances with physiologically acceptable excipients. The preparations according to the invention may contain the combination of active substances 1 and 2 either together in one formulation or in two separate formulations. These formulations which may be used within the scope of the present invention are described in more detail in the next part of the specification.

Inhalable Powders Containing Combinations of Active Substances 1 and 2 According to the Invention The inhalable powders according to the invention may contain 1 and 2 either on their own or in admixture with suitable physiologically acceptable excipients.

If the active substances 1 and 2 are present in admixture with physiologically acceptable excipients, the following physiologically acceptable excipients may be used to prepare these inhalable powders according to the invention: monosaccharides (e.g., glucose or arabinose), disaccharides (e.g., lactose, saccharose, maltose), oligo- and polysaccharides (e.g., dextran), polyalcohols (e.g., sorbitol, mannitol, or xylitol), salts (e.g., sodium chloride or calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 μm and 150 μm, most preferably between 15 μm and 80 μm. It may sometimes seem appropriate to add finer excipient fractions with an average particle size of 1 μm to 9 μm to the excipient mentioned above. These finer excipients are also selected from the group of possible excipients listed hereinbefore. Finally, in order to prepare the inhalable powders according to the invention, micronised active substance 1 and 2, preferably with an average particle size of 0.5 μm to 10 μm, more preferably from 1 μm to 6 μm, is added to the excipient mixture. Processes for producing the inhalable powders according to the invention by grinding and micronizing and by finally mixing the ingredients together are known from the prior art. The inhalable powders according to the invention may be prepared and administered either in the form of a single powder mixture which contains both 1 and 2 or in the form of separate inhalable powders which contain only 1 and 2.

The inhalable powders according to the invention may be administered using inhalers known from the prior art. Inhalable powders according to the invention which contain a physiologically acceptable excipient in addition to 1 and 2 may be administered, for example, by means of inhalers which deliver a single dose from a supply using a measuring chamber as described in U.S. Pat. No. 4,570,630, or by other means as described in DE 36 25 685 A. Preferably, the inhalable powders according to the invention which contain physiologically acceptable excipients in addition to 1 and 2 are packed into capsules (to produce so-called inhalettes) which are used in inhalers as described, for example, in WO 94/28958.

A particularly preferred inhaler for using the pharmaceutical combination according to the invention in inhalettes is shown in FIG. 1.

This inhaler (HANDIHALER®) for inhaling powdered pharmaceutical compositions from capsules is characterized by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut.

If the inhalable powders according to the invention are packed into capsules (inhalers) for the preferred use described above, the quantities packed into each capsule should be 1 mg to 30 mg, preferably 3 mg to 20 mg, more particularly 5 mg to 10 mg of inhalable powder per capsule. These capsules contain, according to the invention, either together or separately, the doses of 1 and 2 mentioned hereinbefore for each single dose.

The following Examples serve to illustrate the present invention further without restricting the scope of the invention to the following embodiments provided by way of example.

FORMULATION EXAMPLES

| Ingredients | μg per capsule |
|---|---|
| 1. Powder for Inhalation | |
| tiotropium bromide monohydrate | 10.8 |
| salmeterol salt (2.1) | 35 |
| lactose | 4954.2 |
| Total | 5000 |
| 2. Powder for Inhalation | |
| tiotropium bromide monohydrate | 21.7 |
| salmeterol salt (2.23) | 75 |
| lactose | 4903.3 |
| Total | 5000 |
| 3. Powder for Inhalation | |
| tiotropium bromide monohydrate | 22.5 |
| salmeterol salt (2.1) | 80.5 |
| lactose | 4897 |
| Total | 5000 |
| 4. Powder for Inhalation | |
| tiotropium bromide × H2O | 22.5 |
| salmeterol salt (2.23) | 95.5 |
| lactose | 4828 |
| Total | 5000 |

We claim:

1. A pharmaceutical composition comprising:
   (a) tiotropium bromide and
   (b) a salmeterol salt having a solubility in water of 0.1 mg/mL or less.

2. A pharmaceutical kit comprising:
   (a) a pharmaceutical composition comprising tiotropium bromide and
   (b) a pharmaceutical composition comprising a salmeterol salt having a solubility in water of 0.1 mg/mL or less.

3. The pharmaceutical composition according to claim 1, wherein the salmeterol salt is an acid addition salt of salmeterol formed with an acid selected from the group consisting of: 2-hydroxy-1-naphthoic acid, 3,5-dichlorosalicylic acid, furan-2-carboxylic acid, 2,5-dihydroxyterephthalic acid, cinnamic acid, triphenylacetic acid, 4-phenylcinnamic acid, biphenyl-2-carboxylic acid, 4-trifluoromethylcinnamic acid, 9-fluorenylideneacetic acid, 3-(2-naphthyl)acrylic acid, 3-(1-naphthyl)acrylic acid, 1-naphthoic acid, 2,6-dichlorobenzoic acid, 3,4-dichlorobenzoic acid, 3,5-dichlorobenzoic acid, 4-bromobenzoic acid, 4-trifluoromethylbenzoic acid, 4-isopropylbenzoic acid, 4-tert-butylbenzoic acid, 3-(3-indolyl)acrylic acid, 2,4-dichlorocinnamic acid, 2,6-dichlorocinnamic acid, 2,5-dimethoxycinnamic acid, 2-trifluoromethylcinnamic acid, 3-trifluoromethylcinnamic acid, 3-chlorocinnamic acid, 3,4-dichlorocinnamic acid, 4-bromocinnamic acid, 4-chlorocinnamic acid, 4-methoxycinnamic acid, 4-fluorocinnarnic acid, 4-isopropylcinnamic acid, 4-tert-butylcinnamic acid, 2,6-difluorocinnamic acid, 2,4-difluorocinnamic acid, 3,4-difluorocinnamic acid, 2,4,5-trifluorocinnamic acid, 3,4,5-trifluorocinnamic acid, 3-methoxysalicylic acid, 4-methoxysalicylic acid, 5-methoxysalicylic acid, 4-methylsalicylic acid, 5-aminosalicylic acid, 3-chlorosalicylic acid, 5-sulfosalicylic acid, 5-acetylsalicylic acid, 3,5-diiodosalicylic acid, isoquinoline-1-carboxylic acid, 9-fluorenecarboxylic acid, 9-fluorenone-1-carboxylic acid, 3,5-diisopropylsalicylic acid, and diflunisal.

4. The pharmaceutical composition according to claim 1, wherein the salmeterol salt is selected from the group consisting of:

4-hydroxy-α$^1$-[[[6-(4-phenylbutoxy)hexyl]amino] methyl]-1,3-benzenedimethanol-4-phenylcinnamate;

4-hydroxy-α$^1$-[[[6-(4-phenylbutoxy)hexyl]amino] metbyl]-1,3-benzenedimethanol-4-trifluoromethylcinnamate;

4-hydroxy-α$^1$-[[[6-(4-phenylbutoxy)hexyl]amino] methyl]-1,3-benzenedimethanol-3,4-dichlorocinnamate;

4-hydroxy-α$^1$-[[[6-(4-pbenylbutoxy)hexyl]amino] methyl]-1,3-benzenedimethanol-2,4-dichlorocinnamate;

4-hydroxy-α$^1$-[[[6-(4-phenylbutoxy)hexyl]amino] methyl]-1,3-benzenedimethanolcinnamate;

4-hydroxy-α$^1$-[[[6-(4-phenylbutoxy)hexyl]amino] methyl]-1,3-benzenedimethanol-3-(2-naphthyl) acrylate;

4-hydroxy-α$^1$-[[[6-(4-phenylbutoxy)hexyl]amino] methyl]-1,3-benzenedimethanol-3-(1-naphthyl) acrylate;

4-hydroxy-α$^1$-[[[6-(4-phenylbutoxy)hexyl]amino] methyl]-1,3-benzenedimethanol-2,6-dichlorocinnamate;

4-hydroxy-α$^1$-[[[6-(4-phenylbutoxy)hexyl]amino] methyl]-1,3-benzenedimethanol-2,5-dimethoxycinnamate;

4-hydroxy-α$^1$-[[[6-(4-phenylbutoxy)hexyl]amino] methyl]-1,3-benzenedimethanol-2-trifluoromethylcinnamate;

4-hydroxy-α¹-[[[6-(4-phenylbutoxy)hexyl]amino]methyl]-1,3-benzenedimethanol-3-trifluoromethylcinnamate;

4-hydroxy-α¹-[[[6-(4-phenylbutoxy)hexyl]amino]methyl]-1,3-benzenedimethanol-3-chlorocinnamate;

4-hydroxy-α¹-[[[6-(4-phenylbutoxy)hexyl]amino]methyl]-1,3-benzenedimethanol-4-bromocinnamate;

4-hydroxy-α¹-[[[6-(4-phenylbutoxy)hexyl]amino]methyl]-1,3-benzenedimethanol-4-chlorocinnamate;

4-hydroxy-α¹-[[[6-(4-phenylbutoxy)hexyl]amino]methyl]-1,3-benzenedimethanol-4-methoxycinnamate;

4-hydroxy-α¹-[[[6-(4-phenylbutoxy)hexyl]amino]methyl]-1,3-benzenedimetbanol-4-fluorocinnamate;

4-hydroxy-α¹-[[[6-(4-phenylbutoxy)hexyl]amino]methyl]-1,3-benzenedimethanol-4-isopropylcinnamate;

4-hydroxy-α¹-[[[6-(4-phenylbutoxy)hexyl]amino]methyl]-1,3-benzenedimethanol-4-tert-butylcinnamate;

4-hydroxy-α¹-[[[6-(4-phenylbutoxy)hexyl]amino]methyl]-1,3-benzenedimethanol-2,4-difluorocinnamate;

4-hydroxy-α¹-[[[6-(4-phenylbutoxy)hexyl]amino]methyl]-1,3-benzenedimethanol-3,4-difluorocinnamate;

4-hydroxy-α¹-[[[6-(4-phenylbutoxy)hexyl]amino]methyl]-1,3-benzenedimethanol-2,4,5-trifluorocinnamate; and 4-hydroxy-α¹-[[[6-(4-phenylbutoxy)hexyl]amino]methyl]-1,3-benzenedimethanol-3,4,5-trifluorocinnamate.

5. The pharmaceutical composition according to claim 1, wherein the salmeterol salt is selected from the group consisting of:

4-hydroxy-α¹-[[[6-(4-phenylbutoxy)hexyl]amino]methyl]-1,3-benzenedimethanol-5-(2,4-difluoropbenyl)salicylate;

4-hydroxy-α¹-[[[6-(4-phenylbutoxy)hexyl]amino]methyl]-1,3-benzenedimethanol-3,5-diisopropylsalicylate;

4-hydroxy-α¹-[[[6-(4-phenylbutoxy)hexyl]amino]methyl]-1,3-benzenedimethanol-4-chlorosalicylate;

4-hydroxy-α¹-[[[6-(4-phenylbutoxy)hexyl]amino]methyl]-1,3-benzenedimethanol-3,5-dichlorosalicylate;

4-hydroxy-α¹-[[[6-(4-phenylbutoxy)hexyl]amino]methyl]-1,3-benzenedimethanol-2,5-dihydroxyterephthalate (base:acid=1:2);

4-hydroxy-α¹-[[[6-(4-phenylbutoxy)hexyl]amino]methyl]-1,3-benzenedimethanol-3-methoxysalicylate;

4-hydroxy-α¹-[[[6-(4-phenylbutoxy)hexyl]amino]methyl]-1,3-benzenedimethanol-4-methoxysalicylate;

4-hydroxy-α¹-[[[6-(4-phenylbutoxy)hexyl]amino]methyl]-1,3-benzenedimethanol-5-methoxysalicylate;

4-hydroxy-α¹-[[[6-(4-phenylbutoxy)bexyl]amino]methyl]-1,3-benzenedimethanol-4-methylsalicylate;

4-hydroxy-α¹-[[[6-(4-phenylbutoxy)hexyl]amino]methyl]-1,3-benzenedimetbanol-5-aminosalicylate;

4-hydroxy-α¹-[[[6-(4-phenylbutoxy)hexyl]amino]methyl]-1,3-benzenedimethanol-3-chlorosalicylate;

4-hydroxy-α¹-[[[6-(4-phenylbutoxy)hexyl]amino]methyl]-1,3-benzenedimethanol-5-sulfosalicylate;

4-hydroxy-α¹-[[[6-(4-phenylbutoxy)hexyl]amino]methyl]-1,3-benzenedimethanol-5-acetylsalicylate; and 4-hydroxy-α¹-[[[6-(4-phenylbutoxy)hexyl]amino]methyl]-1,3-benzenedimethanol-3,5-diiodosalicylate.

6. The pharmaceutical kit according to claim 2, wherein the salmeterol salt is an acid addition salt of salmeterol formed with an acid selected from the group consisting of: 2-hydroxy-1-naphthoic acid, 3,5-dichlorosalicylic acid, furan-2-carboxylic acid, 2,5-dihydroxyterephthalic acid, cinnamic acid, triphenylacetic acid, 4-phenylcinnamic acid, biphenyl-2-carboxylic acid, 4-trifluoromethylcinnamic acid, 9-fluorenylideneacetic acid, 3-(2-naphthyl)acrylic acid, 3-(1-naphthyl)acrylic acid, 1-naphthoic acid, 2,6-dichlorobenzoic acid, 3,4-dichlorobenzoic acid, 3,5-dichlorobenzoic acid, 4-bromobenzoic acid, 4-trifluoromethylbenzoic acid, 4-isopropylbenzoic acid, 4-tert-butylbenzoic acid, 3-(3-indolyl)acrylic acid, 2,4-dichlorocinnamic acid, 2,6-dichlorocinnamic acid, 2,5-dimethoxycinnamic acid, 2-tifluoromethylcinnamic acid, 3-trifluoromethylcinnamic acid, 3-chlorocinnamic acid, 3,4-dichlorocinnamic acid, 4-bromcinnamic acid, 4-chlorocinnamic acid, 4-methoxycinnamic acid, 4-fluorocinnamic acid, 4-isopropylcinnamic acid, 4-tert-butylcinnamic acid, 2,6-difluorocinnamic acid, 2,4-difluorocinnamic acid, 3,4-difluorocinnamic acid, 2,4,5-trifluorocinnamic acid, 3,4,5-trifluorocinnamic acid, 3-methoxysalicylic acid, 4-methoxysalicylic acid, 5-methoxysalicylic acid, 4-methylsalicylic acid, 5-aminosalicylic acid, 3-chlorosalicylic acid, 5-sulfosalicylic acid, 5-acetylsalicylic acid, 3,5-diiodosalicylic acid, isoquinoline-1-carboxylic acid, 9-fluorenecarboxylic acid, 9-fluorenone-1-carboxylic acid, 3,5-diisopropylsalicylic acid, and diflunisal.

7. The pharmaceutical kit according to claim 2, wherein the salmeterol salt is selected from the group consisting of:

4-hydroxy-α¹-[[[6-(4-phenylbutoxy)hexyl]amino]methyl]-1,3-benzenedimethanol-4-phenylcinnamate;

4-hydroxy-α¹-[[[6-(4-phenylbutoxy)hexyl]amino]methyl]-1,3-benzenedimethanol-4-trifluoromethylcinnamate;

4-hydroxy-α¹-[[[6-(4-pbenylbutoxy)hexyl]amino]methyl]-1,3-benzenedimethanol-3,4-dichlorocinnamate;

4-hydroxy-α¹-[[[6-(4-phenylbutoxy)hexyl]amino]methyl]-1,3-benzenedimethanol-2,4-dichlorocinnamate;

4-hydroxy-α¹-[[[6-(4-phenylbutoxy)hexyl]amino]methyl]-1,3-benzenedimethanolcinnamate;

4-hydroxy-α¹-[[[6-(4-phenylbutoxy)hexyl]amino]methyl]-1,3-benzenedimethanol-3-(2-naphthyl)acrylate;

4-hydroxy-α¹-[[[6-(4-phenylbutoxy)hexyl]amino]methyl]-1,3-benzenedimethanol-3-(1-naphthyl)acrylate;

4-hydroxy-α¹-[[[6-(4-phenylbutoxy)hexyl]amino]methyl]-1,3-benzenedimethanol-2,6-dichlorocinnamate;

4-hydroxy-α¹-[[[6-(4-phenylbutoxy)hexyl]amino]methyl]-1,3-benzenedimethanol-2,5-dimethoxycinnamate;

4-hydroxy-α¹-[[[6-(4-phenylbutoxy)hexyl]amino]methyl]-1,3-benzenedimethanol-2-trifluoromethylcinnamate;

4-hydroxy-α¹-[[[6-(4-phenylbutoxy)hexyl]amino]methyl]-1,3-benzenedimethanol-3-trifluoromethylcinnamate;

4-hydroxy-α¹-[[[6-(4-phenylbutoxy)hexyl]amino]methyl]-1,3-benzenedimethanol-3-chlorocinnamate;

4-hydroxy-α¹-[[[6-(4-phenylbutoxy)hexyl]amino]methyl]-1,3-benzenedimethanol-4-bromocinnamate;

4-hydroxy-α¹-[[[6-(4-phenylbutoxy)hexyl]amino]methyl]-1,3-benzenedimethanol-4-chlorocinnamate;

4-hydroxy-α¹-[[[6-(4-phenylbutoxy)hexyl]amino]methyl]-1,3-benzenedimethanol-4-methoxycinnamate;

4-hydroxy-α¹-[[[6-(4-phenylbutoxy)hexyl]amino]methyl]-1,3-benzenedimethanol-4-fluorocinnamate;

4-hydroxy-α¹-[[[6-(4-phenylbutoxy)hexyl]amino]methyl]-1,3-benzenedimethanol-4-isopropylcinnamate;

4-hydroxy-α¹-[[[6-(4-phenylbutoxy)hexyl]amino]methyl]-1,3-benzenedimethanol-4-tert-butylcinnamate;

4-hydroxy-α¹-[[[6-(4-phenylbutoxy)hexyl]amino]methyl]-1,3-benzenedimethanol-2,4-difluorocinnamate;

4-hydroxy-α¹-[[[6-(4-phenylbutoxy)hexyl]amino]methyl]-1,3-benzenedimethanol-3,4-difluorocinnamate;

4-hydroxy-α¹-[[[6-(4-phenylbutoxy)hexyl]amino]methyl]-1,3-benzenedimethanol-2,4,5-trifluorocinnamate; and 4-hydroxy-α¹-[[[6-(4-phenylbutoxy)hexyl]amino]methyl]-1,3-benzenedimethanol-3,4,5-trifluorocinnamate.

8. The pharmaceutical kit according to claim 2, wherein the salmeterol salt is selected from the group consisting of:

4-hydroxy-α¹-[[[6-(4-phenylbutoxy)hexyl]amino]methyl]-1,3-benzenedimethanol-5-(2,4-difluorophenyl)salicylate;

4-hydroxy-α¹-[[[6-(4-phenylbutoxy)hexyl]amino]methyl]-1,3-benzenedimethanol-3,5-diisopropylsalicylate;

4-hydroxy-α¹-[[[6-(4-phenylbutoxy)hexyl]amino]methyl]-1,3-benzenedimethanol-4-chlorosalicylate;

4-hydroxy-α¹-[[[6-(4-phenylbutoxy)hexyl]amino]methyl]-1,3-benzenedimethanol-3,5-dichlorosalicylate;

4-hydroxy-α¹-[[[6-(4-phenylbutoxy)hexyl]amino]methyl]-1,3-benzenedimethanol-2,5-dihydroxyterephthalate (base:acid=1:2);

4-hydroxy-α¹-[[[6-(4-phenylbutoxy)hexyl]amino]methyl]-1,3-benzenedimethanol-3-methoxysalicylate;

4-hydroxy-α¹-[[[6-(4-phenylbutoxy)hexyl]amino]methyl]-1,3-benzenedimethanol-4-methoxysalicylate;

4-hydroxy-α¹-[[[6-(4-phenylbutoxy)hexyl]amino]methyl]-1,3-benzenedimethanol-5-methoxysalicylate;

4-hydroxy-α¹-[[[6-(4-phenylbutoxy)hexyl]amino]methyl]-1,3-benzenedimethanol-4-methylsalicylate;

4-hydroxy-α¹-[[[6-(4-phenylbutoxy)hexyl]amino]methyl]-1,3-benzenedimethanol-5-aminosalicylate;

4-hydroxy-α¹-[[[6-(4-phenylbutoxy)hexyl]amino]methyl]-1,3-benzenedimethanol-3-chlorosalicylate;

4-hydroxy-α¹-[[[6-(4-phenylbutoxy)hexyl]amino]methyl]-1,3-benzenedimethanol-5-sulfosalicylate;

4-hydroxy-α¹-[[[6-(4-phenylbutoxy)hexyl]amino]methyl]-1,3-benzenedimethanol-5-acetylsalicylate; and 4-hydroxy-α¹-[[[6-(4-phenylbutoxy)hexyl]amino]methyl]-1,3-benzenedimethanol-3,5-diiodbsalicylate.

9. The pharmaceutical composition according to one of claims 1 or 3 to 5, wherein the weight ratio of the tiotropium bromide to the salmeterol salt, based on the tiotropium cation to salmeterol free base, is in the range of 1:300 to 30:1.

10. The pharmaceutical composition according to claim 9, wherein the weight ratio of the tiotropium bromide to the salmeterol salt, based on the tiotropium cation to salmeterol free base, is in the range of 1:230 to 20:1.

11. The pharmaceutical composition according to one of claims 1 or 3 to 5, wherein a single application corresponds to a dosage of the tiotropium bromide to the salmeterol salt, based on the tiotropium cation to salmeterol free base, is 0.01 µg to 1000 µg.

12. The pharmaceutical composition according to one of claims 1 or 3 to 5, wherein a single application corresponds to a dosage of the tiotropium bromide to the salmeterol salt, based on the tiotropium cation to salmeterol free base, is 0.1 µg to 200 µg.

13. The pharmaceutical composition according to one of claims 1 or 3 to 5, wherein the pharmaceutical composition is in the form of a powder suitable for inhalation.

14. The pharmaceutical composition according to claim 13, wherein the pharmaceutical composition further comprises a physiologically acceptable excipient selected from the group consisting of: monosaccharides, disaccharides, oligo- and polysaccharides, polyalcohols, and salts.

15. The pharmaceutical composition according to claim 14, wherein the excipient has a maximum mean particle size of up to 250 µm.

16. The pharmaceutical composition according to claim 14, wherein the excipient has a maximum mean particle size of between 10 µm and 150 µm.

17. A capsule containing a pharmaceutical composition according to claim 13.

18. A capsule containing a pharmaceutical composition according to claim 14.

19. A capsule containing a pharmaceutical composition according to claim 15.

20. A capsule containing a pharmaceutical composition according to claim 16.

21. A pharmaceutical composition consisting essentially of:
   (a) tiotropium bromide and
   (b) a salmeterol salt having a solubility in water of 0.1 mg/mL or less, wherein the pharmaceutical composition is in the form of an inhalable powder.

22. A method of treating respiratory complaints in a patient in need of such treatment, the method comprising administering to the patient a therapeutically effective amount of the pharmaceutical composition according to one of claims 1 or 3 to 5.

23. A method of treating asthma or chronic obstructive pulmonary disease (COPD) in, a patient in need of such treatment, the method comprising administering to the patient a therapeutically effective amount of the pharmaceutical composition according to one of claims 1 or 3 to 5.

* * * * *